United States Patent [19]

Douglas et al.

[11] 4,242,339

[45] Dec. 30, 1980

[54] METHOD FOR TREATMENT OF GASTROINTESTINAL SPASMODIC DISEASE CONDITIONS OR SYMPTOMS IN MAMMALS

[75] Inventors: George H. Douglas, Malvern; William L. Studt, Harleysville; Stuart A. Dodson, Lansdale, all of Pa.

[73] Assignee: William H. Rorer, Inc., Fort Washington, Pa.

[21] Appl. No.: 1,636

[22] Filed: Jan. 8, 1979

Related U.S. Application Data

[62] Division of Ser. No. 934,780, Aug. 18, 1978, which is a division of Ser. No. 811,092, Jun. 17, 1977, Pat. No. 4,115,647, which is a division of Ser. No. 671,763, Mar. 30, 1976, Pat. No. 4,058,557.

[51] Int. Cl.$^2$ ............... A61K 31/535; A61K 31/445; A61K 31/42; A61K 31/17

[52] U.S. Cl. .............. 424/248.54; 424/267; 424/272; 424/322

[58] Field of Search ............... 424/322, 248.54, 267, 424/272

[56] References Cited

U.S. PATENT DOCUMENTS

| | | | |
|---|---|---|---|
| 3,539,616 | 11/1970 | Walls | 424/322 X |
| 4,117,165 | 9/1978 | Diamond et al. | 424/322 |

*Primary Examiner*—Frederick E. Waddell
*Attorney, Agent, or Firm*—James A. Nicholson; John C. Smith, Jr.

[57] ABSTRACT

A new class of chemical compounds and their process of preparation is described. These compounds have valuable properties as anti-secretory, anti-spasmodic, anti-ulcerogenic and anti-diarrheal agents.

5 Claims, No Drawings

METHOD FOR TREATMENT OF GASTROINTESTINAL SPASMODIC DISEASE CONDITIONS OR SYMPTOMS IN MAMMALS

This is a division of application Ser. No. 934,780 filed Aug. 18, 1978, now allowed, which in turn is a division of application Ser. No. 811,092 filed June 17, 1977, now U.S. Pat. No. 4,115,647 issued Sept. 19, 1978, which in turn is a division of application Ser. No. 671,763 filed Mar. 30, 1976, now U.S. Pat. No. 4,058,557 issued Nov. 15, 1977.

SUMMARY OF THE INVENTION

This invention describes a new class of chemical compounds and the process for their preparation. This invention further describes valuable pharmaceutical preparations which are effective for producing anti-secretory, anti-spasmodic, anti-ulcerogenic and anti-diarrheal actions. This invention further describes a class of chemical compounds called N-oxygenated amidinoureas and the same possess an effective degree of activity which is capable of producing anti-secretory, anti-spasmodic, anti-ulcerogenic and anti-diarrheal properties in mammals.

BACKGROUND OF THE INVENTION

The pharmaceutical compositions which have been used as anti-ulcerogenic agents have been such as atropine, homatropine, propantheline bromide, dicyclomine hydrochloride and other compounds which are structurally dissimilar to the amidinoureas of this invention. Due to the anticholinergic properties of these compounds they are known to produce undesirable side effects such as mydriasis, xerostomia, cycloplegia and other unwanted effects.

Diarrhea is widespread among the world's population. In certain diseases, this enteric disorder can be the cause of a high degree of morbidity and even mortality.

The narcotic analgesics remain the drugs of choice for treatment of diarrhea and dysentery. This group of drugs, however, has serious disadvantages. They possess the narcotic properties of producing sleep as well as analgesia. They also have physical and psychological dependence liabilities. Morphine and codeine remain two outstanding examples of this group.

In 1957 a meperidine derivative, diphenoxylate, was introduced into therapeutic regimen of diarrhea control. This agent possesses morphine-like as well as anticholinergic properties, both of which may be responsible for its anti-diarrheal actions. Diphenoxylate, because of its narcotic properties, is capable of supporting morphine physical dependence in the monkey. Overdoses in children can lead to symptoms and fatalities that are characteristic of the narcotics, e.g. respiratory depression and reversal of morbidity with nalorphine.

We have found novel amidinoureas which are valuable pharmacologic agents possessing useful anti-secretory, anti-spasmodic, anti-ulcerogenic and anti-diarrheal properties.

We have also found that the compounds of this invention are substantially free of the anticholinergic side-effects which accompany this type of agent.

We have further found a simple and effective method for treating duodenal and peptic ulcers.

We have also found compounds which inhibit pepsin generation.

We have also found that the compounds of this invention have an effective degree of muscle relaxant properties which are capable of reducing uterine spasm.

We have further found compounds of this invention to be useful in controlling premenstrual cramps and dysmenorrhea.

We have also found that administration of the amidinoureas of this invention provide a simple and effective method for the treatment of gastrointestinal, spasmolytic, ulcerogenic and diarrheal disorders.

We have found that the amidinoureas of this invention are conveniently prepared.

We have found that the presence of the N-oxygenated group on the amidinourea moiety reduces the basicity of the molecule by a factor of about 1000 and is thereby valuable in that it reduces any cardiovascular side effects which would be present in compounds not having this feature.

DESCRIPTION AND PREFERRED EMBODIMENTS

This invention describes a novel class of chemical compounds of the formula:

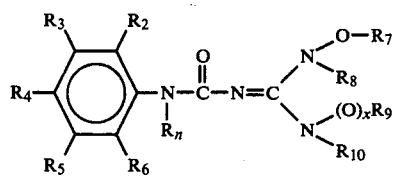

where:
$R_2$, $R_3$, $R_4$, $R_5$ and $R_6$ may be the same or different and are:
hydrogen,
halo,
loweralkyl,
haloloweralkyl,
nitro,
amino,
acylamino,
hydroxy,
aralkyloxy or
loweralkoxy;
$R_n$ is hydrogen or loweralkyl;
$R_7$, $R_8$, $R_9$ and $R_{10}$ may be the same or different and are:
hydrogen,
alkyl,
alkenyl,
alkynyl,
cycloalkyl or
aralkyl;
$R_7$ and $R_8$ together and $R_9$ and $R_{10}$ together may form a 5-7 atom ring which may further include 0-1 hetero atoms of N, O or S;
x is 0-1;
the sum total of carbon atoms present in $R_7$, $R_8$, $R_9$ and $R_{10}$ together is less than twelve; and
the non-toxic acid addition salts thereof.

In any discussion of the true structure of an amidinourea, tautomerism must be considered. It should be clear to anyone skilled in the art that the amidinourea side-chain can be legitimately represented in any one of several tautomeric and geometric modifications.

The total number of possible variations in structure is quite high, but it is true to say that these variations can and, to some extent, do occur when these compounds are in solution.

One form may predominate over another depending upon the degree and location of substitution and on the nature of the solvent. The rates of conversion of one tautomer to another will depend upon the nature of the solvent, the degree of hydrogen bonding permitted, the temperature and possibly other factors (such as pH, trace impurities and the like).

To illustrate what is meant by this, a number of likely structures are here shown for just one of the compounds in this invention.

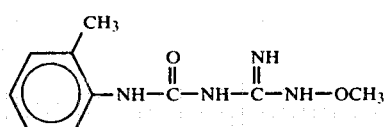
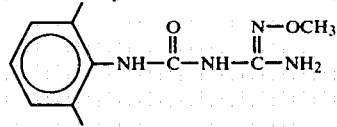
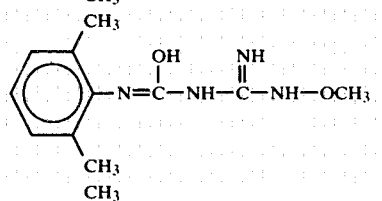
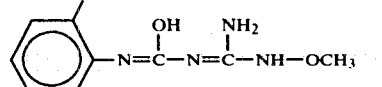
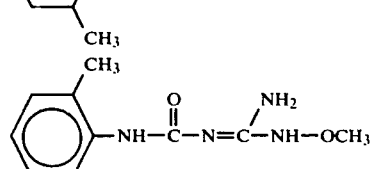
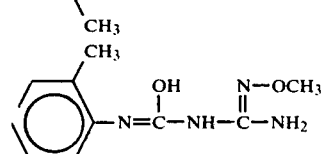
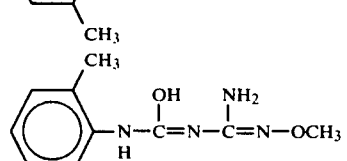
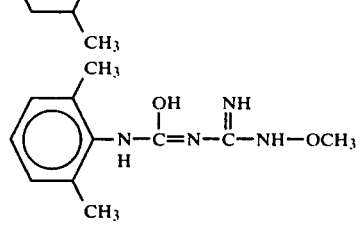

Of course, other types of structures are possible such as those with hydrogen bonding.

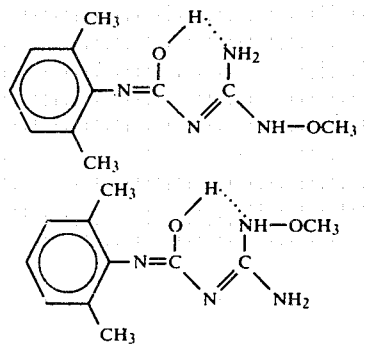

No attempt is made to exhaust the possible structures, for these are legion. The structures given are representative of the kind of phenomenon we are trying to describe and are encompassed within the scope of this invention.

It is predictable that in physiological conditions, any or all of these structures may exist or even predominate at the sites at which these molecules operate.

Tautomerism, of course, by definition only applies to protons and not to other groups. Thus, in the example given, free conversion between structures occurs smoothly by transference of a single proton. At a time where other substituents are concerned, tautomerism is to just that extent ruled out. For example where there are no protons at all because of full substitution, only one structure may be reasonably said to exist such as:

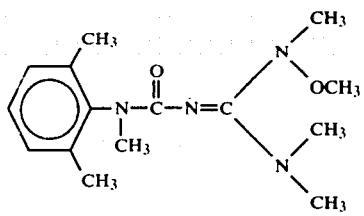

Compounds of this invention which are preferred include those
where:
$R_2$ and $R_6$ are halo,
 loweralkyl,
 haloloweralkyl,
 nitro or
 loweralkoxy;
$R_3$ and $R_5$ are hydrogen;
$R_4$ is hydrogen,
 halo,
 loweralkyl,
 amino,
 acylamino or
 hydroxy;
$R_7$, $R_9$ and $R_n$ are hydrogen or alkyl; $R_7$ and $R_9$ may also be aralkyl;
$R_8$ and $R_{10}$ are hydrogen, loweralkyl, alkenyl or alkynyl; and
$R_7$ and $R_8$ together and $R_9$ and $R_{10}$ together are alkylidenyl; and
x is 0-1.

The more preferred compounds of this invention include those
where:
$R_2$ is halo or loweralkyl;
$R_3$, $R_4$ and $R_5$ are hydrogen;
$R_6$ is loweralkyl,
nitro,
haloloweralkyl,
loweralkoxy or
halo,
$R_7$, $R_9$ and $R_n$ are hydrogen or alkyl; $R_7$ and $R_9$ may also be aralkyl;
$R_8$ and $R_{10}$ are hydrogen or loweralkyl;
$R_7$ and $R_8$ together and $R_9$ and $R_{10}$ together are alkylidenyl; and
x is 0–1.

The most preferred compounds of this invention are those
where:
$R_2$ is chloro,
bromo,
fluoro,
methyl or
ethyl;
$R_3$, $R_4$ and $R_5$ are hydrogen;
$R_6$ is methyl,
ethyl,
nitro,
methoxy,
ethoxy,
chloro,
bromo or
fluoro;
$R_n$ is hydrogen,
methyl or
ethyl, and
$R_8$ and $R_{10}$ are hydrogen,
methyl or
ethyl;
$R_7$ and $R_9$ are hydrogen,
methyl,
ethyl,
propyl,
i-propyl,
butyl,
i-butyl,
sec-butyl,
t-butyl,
pentyl,
hexyl,
heptyl or benzyl; and
x is 0.

A special embodiment of this invention comprises compounds
where:
$R_2$ is chloro,
bromo,
fluoro,
methyl or
ethyl;
$R_3$, $R_4$ and $R_5$ are hydrogen,
$R_6$ is methyl,
ethyl,
nitro,
methoxy,
ethoxy,
chloro,
bromo or
fluoro;
$R_n$ is hydrogen,
methyl or
ethyl, and
$R_7$ and $R_8$ together are trimethylene and tetramethylene;
$R_9$ and $R_{10}$ are hydrogen,
methyl,
ethyl or
together are trimethylene or tetramethylene; and
x is 0.

It is well known in the pharmacological arts that non-toxic acid addition salts of pharmacologically active amine compounds do not differ in activities from their free base. The salts merely provide a convenient solubility factor.

The amines of this invention may be readily converted to their non-toxic acid addition salts by customary methods in the art. The non-toxic salts of this invention are those salts the acid component of which is pharmacologically acceptable in the intended dosages; such salts would include those prepared from inorganic acids, organic acids, higher fatty acids, high molecular weight acids, etc., and include such as:

| | |
|---|---|
| hydrochloric acid, | succinic acid, |
| hydrobromic acid, | glycolic acid, |
| sulfuric acid, | lactic acid, |
| nitric acid, | salicylic acid, |
| phosphoric acid, | benzoic acid, |
| methane sulfonic acid, | nicotinic acid, |
| benzene sulfonic acid, | phthalic acid, |
| acetic acid, | stearic acid, |
| propionic acid, | oleic acid, |
| malic acid, | abietic acid, etc. |

The nomenclature applied to the compounds of this invention is based on the urea moiety as follows:

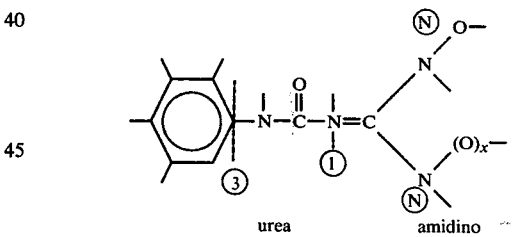

urea   amidino

The term "loweralkyl" refers to an alkyl hydrocarbon group from 1 to 5 carbon atoms which may be straight chained or branched while "alkyl" refers to an alkyl hydrocarbon group which may have as many as ten carbon atoms.

The term "alkenyl" refers to an alkenyl hydrocarbon chain having 3–7 carbon atoms.

The term "alkynyl" refers to an alkynyl hydrocarbon chain having 3–7 carbon atoms.

The term "cycloalkyl" refers to a cycloalkyl group having 3–7 carbon atoms.

The "loweralkoxy" radical signifies an alkoxy group containing from 1 to about 5 carbon atoms which may be straight chained or branched.

The preferred "aryl" group is phenyl.

The preferred "aralkyl" groups are benzyl and phenethyl.

The preferred "haloloweralkyl" group is trifluoromethyl.

The compounds of this invention may be prepared by the following general synthesis.

Condensation of a substitutedphenyl isocyanate (prepared from an aniline and phosgene in the customary manner) with an N-oxygenated guanidine results in a 3-substitutedphenyl-1-(N-oxyamidino)urea. The reaction is carried out in a polar medium using solvents such as dimethylformamide, tetrahydrofuran, etc.

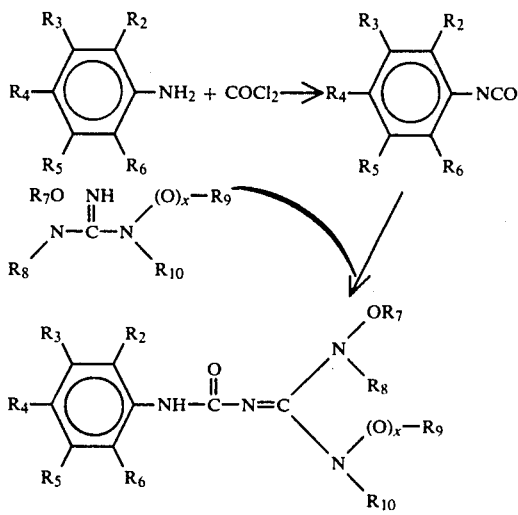

When it is desired to have $R_n$ substitution at the N-3 position, the starting material of course will be aniline having N-alkyl substitution. Reaction with phosgene results in the carbamoyl chloride which is then reacted with the N-oxygenated guanidine to prepare the 3-substitutedphenyl-3-alkyl-1-(N-oxyamidino)urea.

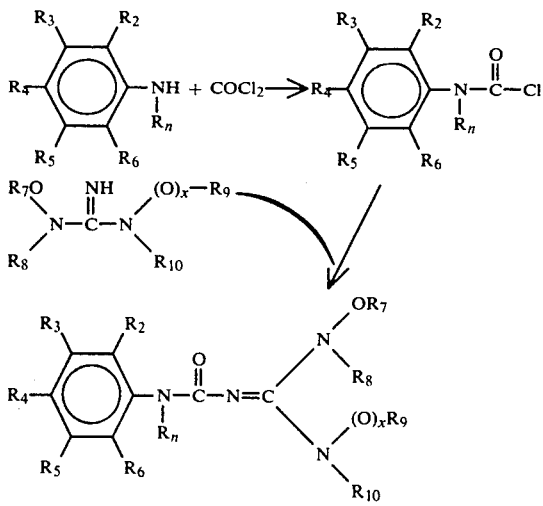

The guanidine starting materials are either known or may be prepared by the following general reactions. Reaction of an alkyl halide with N-hydroxyphthalimide in the presence of base followed by acid hydrolysis results in the oxyamine. This condensation may be carried out in the presence of an inorganic, alkoxide or tertiary amine base (preferably triethylamine is used) in a polar medium (preferably alcohol or DMF), and at room temperature. The acid hydrolysis is carried out in strong inorganic acid conditions or hydrazine in ethanol; however acetic acid/conc. HCl is preferred. The hydrolysis results in the alkoxyamine and phthalic acid and isolation may be carried out in the normal manner with separation by the hydrochloride salt preferred. When other $R_7$, $R_8$, $R_9$ and $R_{10}$ groups other than alkyl are preferred, then the starting halide would be the appropriate alkenyl halide, alkynyl halide, cycloalkyl halide or aralkyl halide.

Reaction of the oxyamine with a substituted pseudothiouronium salt in aqueous or alcoholic solution gives the N-oxygenated guanidine. This may be carried out at any convenient temperature between room temperature and reflux of the reaction mixture.

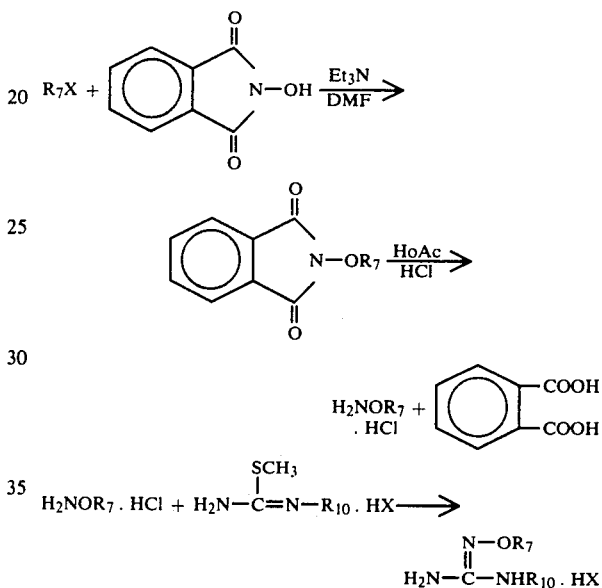

where HX is a mineral acid.

When an N-hydroxyurethan is reacted with two equivalents of an alkyl halide in alcoholic basic medium (preferably alcoholic KOH) then the corresponding N-alkyl-N-oxyurethan is prepared. This may then be hydrolyzed to the amine and reacted as above with a suitable pseudothiouronium salt.

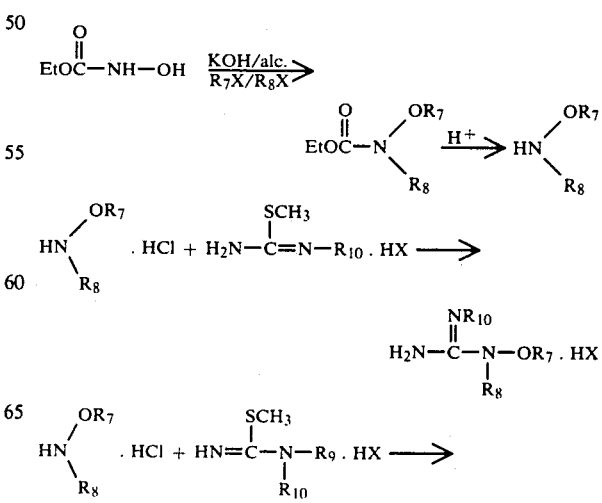

-continued

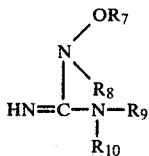

When it is desired to have two alkoxy groups present in the guanidine, then the pseudothiouronium used should be an N-oxy pseudothiouronium salt which is reacted with the alkoxyamine

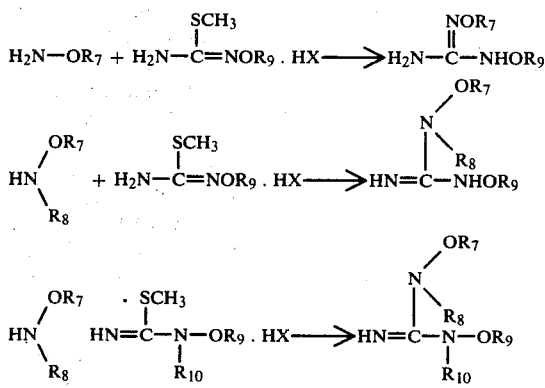

We have found that the compounds of this invention have useful antiulcerogenic properties. Further they have an effective degree of gastric anti-secretory activity and effectively reduce the volume and the acidity of the gastric fluid in humans and mammals. Still further, these compounds produce a considerable spasmolytic action on the gastrointestinal musculature, i.e., they reduce the peristaltic action of the gastrointestinal musculature which is manifested by a delay in gastric emptying time.

Until now, the known antiulcerogenic compounds which showed gastric anti-secretory and gastrointestinal spasmolytic action have included such agents as atropine, homatropine, propantheline, dicyclomine, etc. These compounds, however, cause accompanying undesirable anticholinergic properties such as mydriasis, xerostomia, cyclopegia, etc.

We have found that the N-oxygenated amidinoureas of this invention are particularly useful as anti-secretory, anti-spasmodic and anti-ulcerogenic agents because they are essentially devoid of these unwanted effects.

In particular the N-oxygenated amidinoureas as herein described are useful in the treatment of such ulcerogenic disorders and diseases as duodenal ulcer and peptic ulcer.

The instant compounds may be used alone or in combination with other known antacids such as aluminum hydroxide, magnesium hydroxide, magnesium trisilicate, aluminum glycinate, calcium carbonate and the like.

For all these purposes, N-oxygenated amidinoureas of this invention can be normally administered orally or parenterally. Orally they may be administered as tablets, aqueous or oily suspension, dispersible powders or granules, emulsions, hard or soft capsules, or syrups or elixirs. The term parenteral as used herein, includes subcutaneous injection, intravenous, intramuscular or intrasternal injection or infusion techniques.

Compositions intended for oral use may be prepared according to any method known to the art for the manufacture of pharmaceutical compositions and such compositions may contain one or more agents selected from the group consisting of sweetening agents, flavoring agents, coloring agents and preserving agents, in order to provide a pharmaceutically elegant and palatable preparation.

Further, these compounds may be tableted or otherwise formulated so that for every 100 parts by weight of the composition, there are present between 5 and 95 parts by weight of the active ingredient. The dosage unit form will generally contain between about 1 mg. and about 500 mg. of the active ingredients of this invention. The preferred unit dose is between about 10 mg. and about 100 mg.

The dosage regimen in carrying out the methods of this invention is that which insures maximum therapeutic response until improvement is obtained and thereafter the minimum effective level which gives relief. Thus, in general, the dosages are those that are therapeutically effective in the treatment of ulcerogenic disease conditions or symptoms, such as duodenal and peptic ulcer. In general, the daily dose can be between about 0.1 mg/kg and 150 mg/kg (preferably in the range of 1–100 mg/kg/day), bearing in mind, of course, that in selecting the appropriate dosage in any specific case, consideration must be given to the patient's weight, general health, age and other factors which may influence response to the drug.

Various tests in animals have been carried out to show the ability of the compounds of this invention to exhibit reactions that can be correlated with anti-ulcerogenic activity in humans. These tests involve such as the effect of the N-oxygenated amidinoureas on gastric secretion and gastro-intestinal spasm. It has been found that the compounds of this invention when tested in the above variety of situations show a marked activity.

One such test is the gastric secretion test. This test is carried out as follows: Shay rats are fasted for 4–8 hours, and water is given ad lib. The rats are selected at random and separated into groups of 10. The animals are treated intraduodenally (I.D.) with the test compound or the vehicle immediately subsequent to the ligation of the stomach at the pyloric sphincter. The animals are sacrificed with chloroform at 4 hours post-drug administration, the stomach is removed and its contents are assayed for volume, pH and total acids.

A second gastric secretion test is carried out on dogs. This is outlined in the Handbook of Physiology, Section 6: Alimentary Canal, Volume II: Secretion, American Physiology Society, Washington, D.C., 1967.

It has been found that the compounds of this invention when subjected to the above gastric secretion tests display a marked ability to decrease gastric volume and gastric acidity. These tests are known to correlate well with gastric activity in humans and is a standard test used to determine anti-secretory properties.

To determine the anti-ulcer effectiveness, the following test is employed: Shay rats are fasted for 4–8 hours, and water is given ad lib. The rats are selected at random and separated into groups of ten. The animals are treated intraduodenally (I.D.) with the test compound or the vehicle immediately subsequent to the ligation of the stomach at the pyloric sphincter. The animals are sacrificed with chloroform at 22 hours post-drug administration, the stomach is removed and checked for ulcers which are then rated along with the survival rate.

A second test employed involves cysteamine induced ulcers following the procedure as outlined in *Digestion* 11 198-214 (1974) A. Robert, J. E. Nezamis, C. Lancaster and J. N. Badalamenti.

Uterine motility may be determined by the method described in the *Can. J. Physical Pharmacal* 49: 988-998, 1971 Ivo Polecek and Edwin E. Daniel.

Pepsin inhibition may be determined following the methods of Chiang, L. et al., *Proc. Sec. Expth. Biol. Med.*, 22: 700, 1966 and Anson, M. L. and Mirsky, A. E., *J. Gen. Physical* 16: 159,1932.

In view of the results of these tests, the pharmacological data clearly indicates that the amidinoureas of this invention can be considered to be effective anti-ulcerogenic agents having active gastric anti-secretory and anti-spasmodic properties which are substantially free of anti-cholinergic side effects and having a low toxicity.

The compounds described in this application are also useful anti-diarrheal agents. For these purposes they can be administered orally, parenterally or rectally. Administration by the oral route is preferred. Orally, these compounds may be administered in tablets, hard or soft capsules, aqueous or oily suspensions, dispersible powders or granules, emulsions, syrups or elixers. The optimum dosage, of course, will depend on the particular compound being used and the type and severity of the condition being treated. In any specific case the appropriate dosage selected will further depend on factors of the patient which may influence response to the drug; for example, general health, age, weight, etc. of the subject being treated.

Although the optimum quantities of the compounds of this invention to be used as anti-diarrheal agents will depend on the compound employed and the particular type of disease condition treated, oral dose levels of preferred compounds when administered to a mammal in dosages of 0.01 to 500 milligrams per kilogram of body weight per day are particularly useful. The preferred range is 0.05 to 200 mg/kg. Comparative dosages may be used in parenteral or rectal administration.

Compositions intended for oral use may be prepared according to methods known to the art for the manufacture of pharmaceutical compositions. Such compositions may contain one or more agents selected from the group consisting of sweetening agents, flavoring agents, coloring agents, preserving agents, etc. in order to provide a pharmaceutically elegant and palatable preparation.

Further the active amidinourea may be administered alone or in admixture with other agents having the same or different pharmacological properties.

The composition may contain such selected excipients such as inert diluents such as calcium carbonate, lactose, etc.; granulating and disintegrating agents such as maize starch, alginic acid, etc.; lubricating agents such as magnesium stearate, etc.; binding agents such as starch gelatin, etc.; suspending agents such as methylcellulose, vegetable oil, etc.; dispersing agent such as lecithin, etc.; thickening agents such as beeswax, hard paraffin, etc.; emulsifying agents such as naturally-occurring gums, etc.; non-irritating excipients such as cocoa butter, polyethylene glycols, etc.; and the like. Further, in formulating these compounds for every 100 parts by weight of the composition, there may be present between 5 and 95 parts by weight of the active ingredient. The dosage unit form will generally contain between 0.1 mg. and about 500 mg. of the active ingredients of this invention. The preferred unit dose is between 1 mg. and about 50 mg. The compositions may be taken 1-8 times daily depending on the dosage unit required.

Various tests can be carried out in animal models to show the ability of the amidinoureas of this invention to exhibit reactions that can be correlated with anti-diarrheal activity in humans. The following tests show the ability of the compounds of this invention to inhibit diarrhea in animals and are known to correlate well with anti-diarrheal activity in humans. These are considered to be standard tests used to determine anti-diarrhea properties. This correlation can be shown by the activities of compounds known to be clinically active. In view of the results of these tests, the amidinoureas of this invention can be considered to be anti-diarrheal agents.

1. Fecal output in rat:-The oral $ED_{50}$ (that dose which would be expected to reduce fecal output by 50%) is determined by a method described by Bass et al., 1972. Briefly, the method involves dosing the rats and collecting the fecal output over an 8 hour period (4 PM-12 midnight) with the room darkened starting at 4:30 P.M.

Ref:-Bass, P., Kennedy, J. A. and Willy, J. N.: Measurement of fecal output in rats. Am. J. Dig. Dis. 10: 925-928, 1972.

2. Castor oil test in mice:-Groups of mice are orally dosed with test compound and half hour later all mice given 0.3 ml. of castor oil. Three hours after castor oil administration, all mice are checked for diarrhea and the dose of testing compound which protected 50% of mice for diarrhea is the $ED_{50}$ dose.

3. Castor oil test in rats:-The test is conducted according to Nie megeers et al. 1972. The rat is orally dosed with graded doses of test compound. One hour after dosing, each animal is challenged with 1 ml. of castor oil orally. Fecal output is examined 1, 2, 3, 4, 6, and 8 hours after castor oil. Absence of diarrhea is criterion of drug effectiveness.

Ref:-Niemegeers C. J. E., Lenaerts, F. M. and Janssen, P. A. J. Difenoxine, a potent, orally active and safe anti-diarrheal agena in rats. Arzneim-Forscth (Drug Res.) 22, 516-1518, 1972.

EXAMPLE 1

1-(2,6-Dimethylphenyl)-3-methoxyamidinourea Hydrochloride

To a suspension of 12.0 g. (0.11 mole) of methoxyguanidine hydrochloride in tetrahydrofuran (100 ml.) is added 8.8 g. (0.11 mole) of fifty percent (w/w) aqueous sodium hydroxide. After one hour of stirring, 5.0 g. of anhydrous sodium sulfate is added and the mixture is stirred for an additional hour. A solution of 14.7 g. (0.1 mole) of 2,6-dimethylphenylisocyanate in tetrahydrofuran (30 ml.) is added dropwise after which the mixture is stirred at room temperature overnight. The tetrahydrofuran is removed under vacuum and the residue partitioned between water and chloroform. The layers are separated and the aqueous layer extracted with chloroform (4×100 ml.). The combined organic extracts are washed with water (1×50 ml.), dried over anhydrous magnesium sulfate and filtered. The filtrate is acidified with ethereal HCl and the solvents removed in vacuo to give a brown oil which is crystallized from acetonitrile to give 1-(2,6-dimethylphenyl)-3-methoxyamidinourea hydrochloride, m.p. 170°–1° C.

EXAMPLE 2

1-(2,6-Diethylphenyl)-3-(N-methoxy-N'-methylamidino)urea Hydrochloride

To a suspension of 10.0 g. (30.0 mmol) of N-methoxy-N'-methyl guanidine picrate in tetrahydrofuran (60 ml.) are added 2.4 g. (30.0 mmol) of fifty percent (w/w) aqueous sodium hydroxide and the mixture stirred for 1½ hours. Five (5.0) grams of anhydrous sodium sulfate is added and the mixture stirred for an additional one-half hour. To this mixture is added a solution of 4.8 g. (30.0 mmol) of 2,6-diethylphenylisocyanate in tetrahydrofuran (20 ml.) and the mixture stirred over night. The mixture is partitioned between chloroform and water and the layers are separated. The chloroform layer is washed well with dilute aqueous sodium hydroxide until most of the color is removed then dried over anhydrous magnesium sulfate, filtered and concentrated to give an oil which is dissolved in methanol and acidified with methanolic hydrochloric acid. The methanol is removed under vacuum to give a gummy foam which is crystallized from methanol/ethyl acetate to give 1-(2,6-diethylphenyl)-3-(N-methoxy-N'-methylamidino)urea hydrochloride, m.p. 159.5°–160.5° C.

EXAMPLE 3

A. N-propoxyphthalimide A mixture of 212 g. of N-hydroxyphthalimide, 132 g. of triethylamine, 160 g. of 1-bromopropane and 500 ml. of dimethylformamide is stirred overnight. The reaction mixture is poured into 4.5 liters of water and is stirred at ice temperature for 1½ hours. The solid is removed by filtration, washedwith water and dried in vacuo to give N-propoxyphthalimide, m.p. 51°–3° C.

B. Propoxyamine hydrochloride A solution of 219 g. of N-propoxyphthalimide in a mixture of 600 ml. of acetic acid and 300 ml. of concentrated hydrochloric acid is brought to a gentle boil and kept there for thirty minutes. The mixture is cooled and filtered to remove phthalic acid. The filtrate is evaporated to dryness and the residue partitioned between water and ether. The aqueous layer is washed with ether (2×250 ml.), filtered and evaporated in vacuo. The resultant white solid is dissolved in absolute ethanol and again evaporated in vacuo to give, after drying, crystalline propoxyamine hydrochloride, m.p. 146°–9° C.

C. N-propoxyguanidine hydrochloride To a solution of 113.2 g. of propoxyamine hydrochloride in 200 ml. of ice cold water there is added 81.2 g. of 50% aqueous sodium hydroxide solution. The mixture is stirred for thirty minutes and 141.0 g. of S-methyl-2-thiopseudourea sulfate and 200 ml. of water are added. The mixture is stirred at room temperature for two hours and then heated to reflux for one hour. The mixture is treated with 81.2 g. of 50% aqueous sodium hydroxide filtered and evaporated in vacuo. The residue is slurried in 200 ml. of absolute ethanol, the suspension filtered and the filtrate evaporated to an oil. The crude oil is dissolved in 300 ml. of chloroform, the mixture is cooled and filtered to give a clear solution of the guanidine free base. The chloroform solution is made acidic with methanolic hydrogen chloride and then evaporated in vacuo to give propoxyguanidine hydrochloride as a clear viscous oil (m.p. of picrate 179°–80° C.).

This procedure is used for making those oxyamines not available commercially.

EXAMPLE 4

A. Benzyloxyguanidine To a solution of 30.0 g. (0.12 moles) of S-methylthiouronium sulfate in 200 ml. of $H_2O$ there is added a solution of 24.6 g. (0.20 moles) of benzyloxyamine in 250 ml. of 95% ethanol. The mixture is stirred for 72 hours at room temperature. The clear solution is heated at reflux for two hours under a stream of nitrogen. The solvents are removed in vacuo and the residue is treated with 300 ml. of isopropanol. The solid is removed by filtration and dissolved in 300 ml. of water. The solution is made basic with 90 ml. of 10% aqueous sodium hydroxide. The precipitate is collected, washed with water and dried to give benzyloxyguanidine, m.p. 104°–5° C.

B. 1-(2,6-dimethylphenyl)-3-benzyloxyamidinourea hydrochloride To a solution of 9.20 g. (0.056 moles) of benzyloxyguanidine in 100 ml. of tetrahydrofuran there is added dropwise a solution of 8.30 g. (0.056 moles) of 2,6-dimethylphenylisocyanate in 100 ml. of tetrahydrofuran. After stirring for 2 hours the solvent is removed in vacuo and the residue partitioned between water and chloroform. The chloroform is dried over sodium sulfate, filtered and acidified with saturated methanolic hydrogen chloride. The solvents are removed in vacuo and the resultant foam crystallized from 200 ml. of hot ethyl acetate to give 1-(2,6-dimethylphenyl)-3-benzyloxyamidinourea hydrochloride, m.p. 162°–3° C.

C. 1-(2,6-dimethylphenyl)-3-hydroxyamidinourea hydrochloride To a solution of 6.0 g. (0.017 moles) of 1-(2,6-dimethylphenyl)-3-benzyloxyamidinourea in 160 ml. of absolute ethanol there is added 1.0 g. of 5% Pd/carbon and then 1 ml. of saturated ethanolic hydrogen chloride. The mixture is hydrogenated at room temperature and atmospheric pressure until one equivalent of hydrogen is taken up (1 hour). The suspension is filtered through a bed of celite and the filtrate evaporated to an off-white solid. The solid is recrystallized from 150 ml. of 7:1 acetonitri e:methanol to give 1-(2,6-dimethylphenyl)-3-hydroxyamidinourea hydrochloride, m.p. 191°–2° C.

EXAMPLE 5

A. N-Carbethoxyisooxazolidine Trimethylene dibromide (40.4 g; 0.4 mole) and an ethanolic solution (224 ml.) containing potassium hydroxide (22.4 g.; 0.4 mole) are boiled together on a steam bath for six hours. The ethanol is removed by distillation and the residue triturated with ether (3×100 ml.). The combined ether washes are dried over anhydrous magnesium sulfate, filtered and concentrated to give a liquid which is vacuum distilled to give N-carbethoxyisooxazolidine, b.p. 103° C./13 mm.

B. Isooxazolidine Hydrochloride A mixture of 20.5 g. (0.14 moles) of N-carbethoxyisooxazolidine and 18% aqueous hydrochloric acid (100 ml) are refluxed on a steam bath for two hours. After cooling, the solution is extracted with ether (1×30 ml.) and evaporated to dryness under reduced pressure, the last traces of water being removed by evaporation with absolute ethanol. The residue is crystallized from ethanol/ether to give Isooxazolidine hydrochloride, m.p. 124°–5° C.

C. N-amidino-isooxazolidine sulfate To 14.5 g. (0.13 mole) of isooxazolidine hydrochloride in water (100 ml.) is added 10.4 g. (0.13 mole) of fifty percent (w/w) aqueous sodium hydroxide and the mixture stirred for fifteen minutes. To this solution is added 18.1 g. (0.065 moles) of 2-methyl-2-thiopseudourea sulfate and the entire mixture stirred under a stream of nitrogen overnight. The mixture is refluxed for 1½ hours, then filtered while still hot. The water is removed under vacuum to give a semi-solid residue which is triturated with hot isopropanol (3×100 ml.). The isopropanol is removed under vacuum to give an oil which is crystallized from isopropanol to give N-amidinoisooxazolidine sulfate.

D. N-[(2,6-Dimethylphenylcarbamoyl)amidino] isooxazolidine Hydrochloride To 2.9 g. (36.0 mmol) of fifty percent (w/w) sodium hydroxide suspended in tetrahydrofuran (50 ml.) is added 6.0 g. (18.0 mmol) of N-amidinoisooxazolidine sulfate and the mixture stirred for one hour. Five (5.0) grams of anhydrous sodium sulfate are added and the mixture stirred for an additional hour. To this mixture are added 5.4 g. (36.0 mmol) of 2,6-dimethylphenylisocyanate and the mixture stirred for three hours. Thin layer chromatography (ethyl acetate) showed no starting isocyanate so the tetrahydrofuran is removed under vacuum. The residue is partitioned between water and chloroform. The layers are separated and the aqueous layer extracted with chloroform (1×100 ml.). The combined chloroform extracts are dried over anhydrous magnesium sulfate, filtered and concentrated to give an oil which is dissolved in methanol and acidified (pH=1) with methanolic hydrochloric acid. The methanol is removed to give an oil which is triturated with diethyl ether to give a solid which is crystallized from tetrahydrofuran/hexane to give N-[(2,6-dimethylphenylcarbamoyl)amidino] isooxazolidine hydrochloride, m.p. 147°-8° C.

EXAMPLE 6

N,N'-dimethoxyguanidine

To a solution of 50.1 g. of methoxyamine hydrochloride in 200 ml. of ice cold water there is added 48.0 g. of 50% aqueous sodium hydroxide. The mixture is stirred for thirty minutes and there is added 149.5 g. of N-methoxy-S-methylthiouronium iodide and 100 ml. of water. The mixture is stirred at room temperature for 72 hours and then heated at reflux for 3 hours. The mixture is cooled and treated with 48.0 g. of 50% aqueous sodium hydroxide. After stirring for thirty minutes, the solution is evaporated to dryness in vacuo. The residue is triturated with 200 ml. of absolute ethanol. The suspension filtered and the filtrate evaporated in vacuo. The residue dissolved in 150 ml. of chloroform, the mixture cooled and filtered. The clear filtrate evaporated to a clear viscous oil, N,N'-dimethoxyguanidine, m.p. of picrate 160°-2° C.

EXAMPLE 7

Compounds of this invention which are preferred include:
  1-(2,6-dimethylphenyl)-3-methoxyamidinourea hydrochloride
  1-(2,6-diethylphenyl)-3-methoxyamidinourea succinate
  1-(2-bromo-6-methylphenyl)-3-methoxyamidinourea hydrochloride
  1-(2-chloro-6-methylphenyl)-3-methoxyamidinourea hydrochloride
  1-(2,6-dimethylphenyl)-3-ethoxyamidinourea hydrochloride
  1-(2-chloro-6-methyl)-3-ethoxyamidinourea hydrochloride
  1-(2,6-dimethylphenyl)-3-n-butoxyamidinourea hydrochloride
  1-(2,6-dimethylphenyl)-3-n-propoxyamidinourea hydrochloride
  1-(2,6-diethylphenyl)-3-(N-methoxy-N'-methylamidino)urea hydrochloride
  1-(2-chloro-6-methylphenyl)-3-(N-methoxy-N'-methylamidino)urea hydrochloride
  1-(4-bromo-2,6-diethylphenyl)-3-methoxyamidinourea hydrochloride
  1-(4-bromo-2-chloro-6-methylphenyl)-3-methoxyamidinourea hydrochloride
  1-(2,6-diethylphenyl)-3-ethoxyamidinourea succinate
  1-(4-bromo-2,6-dimethylphenyl)-3-methoxyamidinourea hydrochloride
  1-(2,6-diethyl-4-nitrophenyl)-3-methoxyamidinourea hydrochloride
  N-[(2,6-dimethylphenylcarbamoyl)amidino] isooxazolidine hydrochloride
  1-(2-chloro-6-methylphenyl)-3-n-butoxyamidinourea hydrochloride
  1-(1-naphthyl)-3-methoxyamidinourea hydrochloride
  1-(2,6-diethylphenyl)-3-n-propoxyamidinourea succinate
  1-(2,6-dibromo-4-ethylphenyl)-3-methoxyamidinourea hydrochloride
  1-(4-amino-2,6-diethylphenyl)-3-methoxyamidinourea dihydrochloride
  1-(2,6-dimethylphenyl)-3-hydroxyamidinourea hydrochloride
  1-(2,6-dimethylphenyl)-3-benzyloxyamidinourea hydrochloride
  N-[(2,6-dimethylphenylcarbamoyl)amidino] isooxazine hydrochloride
  1-(2,6-diethylphenyl)-3-n-butoxyamidinourea succinate
  N-[(2,6-diethylphenylcarbamoyl)amidino] isooxazine hydrochloride
  1-(2-chloro-6-methylphenyl)-3-n-propoxyamidinourea hydrochloride

We claim:
1. The method for the treatment of gastrointestinal spasms in a mammal comprising administering thereto between 0.1 mg/kg. and 150 mg/kg. of an effective dose of a compound of the formula:

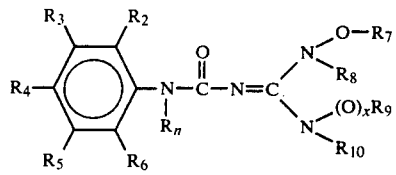

where:
  $R_2$, $R_3$, $R_4$, $R_5$ and $R_6$ may be the same or different and are:
    hydrogen,
    halo,
    loweralkyl,
    haloloweralkyl,
    nitro,
    amino,
    acylamino,
    hydroxy,
    aralkyloxy or
    loweralkoxy,
  $R_n$ is hydrogen or loweralkyl;

R₇, R₈, R₉ and R₁₀ may be the same or different and are:
hydrogen,
alkyl,
alkenyl,
alkynyl,
cycloalkyl or
aralkyl;
x is 0-1;
the sum total of carbon atoms present in R₇, R₈, R₉ and R₁₀ together is less than twelve; and
the non-toxic acid addition salts thereof.

2. The method of claim 1 wherein:
R₂ and R₆ are
halo,
loweralkyl,
haloloweralkyl, p2 nitro or
loweralkoxy;
R₃ and R₅ are hydrogen;
R₄ is
hydrogen,
halo,
loweralkyl,
amino,
acylamino or
hydroxy;
R₇, R₉ and $R_n$ are hydrogen or alkyl;
R₇ and R₉ may also be aralkyl;
R₈ and R₁₀ are
hydrogen,
loweralkyl,
alkenyl or
alkynyl;
x is 0-1.

3. The method of claim 2 wherein:
R₂ is halo or loweralkyl;
R₃, R₄ and R₅ are hydrogen;
R₆ is
loweralkyl,
nitro,
haloloweralkyl,
loweralkoxy or
halo;
R₇, R₉ and $R_n$ are hydrogen or alkyl;
R₇ and R₉ may also be aralkyl; and
R₈ and R₁₀ are hydrogen or loweralky; and
x is 0-1.

4. The method of claim 3 wherein:
R₂ is
chloro,
bromo,
fluoro,
methyl or
ethyl;
R₃, R₄ and R₅ are hydrogen;
R₆ is
methyl,
ethyl,
nitro,
methoxy,
ethoxy,
chloro,
bromo or
fluoro;

$R_n$ is
hydrogen,
methyl or
ethyl,
R₈ and R₁₀ are
hydrogen,
methyl or
ethyl;
R₇ and R₉ are
hydrogen,
methyl,
ethyl,
propyl,
i-propyl,
butyl,
i-butyl,
sec-butyl,
t-butyl,
pentyl,
hexyl,
heptyl, or
benzyl; and
x is 0.

5. The method of treatment of diarrhea in a mammal comprising administering thereto between 0.1 mg/kg. and 150 mg/kg. of an effective dose of a compound of the formula:

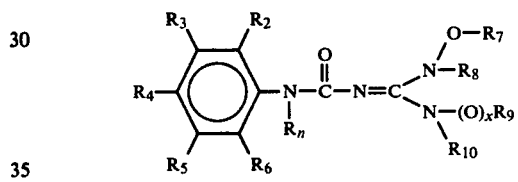

where:
R₂ is
chloro,
bromo,
fluoro,
methyl or
ethyl;
R₃, R₄ and R₅ are hydrogen,
R₆ is
methyl,
ethyl,
nitro,
methoxy,
ethoxy,
chloro,
bromo or
fluoro;
$R_n$ is
hydrogen,
methyl or
ethyl,
R₇ and R₈ together are trimethylene or tetramethylene;
R₉ and R₁₀ are
hydrogen,
methyl,
ethyl or
together are trimethylene or tetramethylene; and
x is 0.

* * * * *